US005514095A

United States Patent [19]
Brightbill et al.

[11] Patent Number: 5,514,095
[45] Date of Patent: May 7, 1996

[54] APPARATUS FOR HEATING, FILTERING AND ELIMINATING GAS FROM BIOLOGICAL FLUIDS

[75] Inventors: Jerry R. Brightbill, Newton; Gary R. Stacey, Marshfield, both of Mass.

[73] Assignee: Haemonetics Corporation, Braintree, Mass.

[21] Appl. No.: 222,649

[22] Filed: Apr. 4, 1994

[51] Int. Cl.$^6$ .................................................. A61M 1/14
[52] U.S. Cl. ............................................................ 604/113
[58] Field of Search .................................. 604/113, 114, 604/122–126; 128/DIG. 3; 607/96, 104–106; 165/67, 156, 163; 422/44–48

[56] References Cited

U.S. PATENT DOCUMENTS

| | | |
|---|---|---|
| 2,124,293 | 7/1938 | Goldstein . |
| 4,065,264 | 12/1977 | Lewin ................................. 23/258.5 |
| 4,138,288 | 2/1979 | Lewin ................................. 195/1.8 |
| 4,168,745 | 9/1979 | Lastinger ............................ 165/164 |
| 4,249,923 | 2/1981 | Walda . |
| 4,402,361 | 9/1983 | Dominguez ......................... 165/156 |
| 4,559,999 | 12/1985 | Servas et al. ....................... 165/156 |
| 4,684,508 | 8/1987 | Sutherland ........................... 422/46 |
| 4,734,091 | 3/1988 | Boyle et al. . |
| 4,735,775 | 4/1988 | Leonard et al. ..................... 422/46 |
| 4,759,749 | 7/1988 | Verkaart ............................. 604/113 |
| 4,878,537 | 11/1989 | Verkaart ............................. 165/156 |
| 4,900,308 | 2/1990 | Verkaart ............................. 604/126 |
| 4,919,134 | 4/1990 | Streeter . |
| 5,063,994 | 11/1991 | Verkaart ............................. 165/154 |
| 5,097,898 | 3/1992 | Verkaart ............................. 165/154 |
| 5,270,005 | 12/1993 | Raible ................................. 422/46 |
| 5,312,589 | 5/1994 | Reeder et al. ....................... 422/45 |

FOREIGN PATENT DOCUMENTS

| | | |
|---|---|---|
| 0552090 | 7/1993 | European Pat. Off. . |
| 9104758 | 4/1991 | WIPO . |
| 9506506 | 3/1995 | WIPO . |

OTHER PUBLICATIONS

"Straight Shot—A Straight–Forward Approach to Cardioplegia Delivery," brochure by Gish Biomedical, Inc. (1993, Nov.).

"AutoVent–SV™ Autoventing Blood Filter," brochure by Pall Biomedical Products Corp., (1991).

"R.I.S.® Rapid Infusion System," Owner's Operating and Maintenance Manual, Haemonetics® Corporation, (Publication Code LP), (1992, Oct.).

U.S. Patent Application Ser. No. 07/080,775 filed on Aug. 3, 1987 by Gary R. Stacey and Wesley H. Verkaart entitled "Blood Compatible Heat Exchanger," .

Ocular Hypothermia: Anterior Chamber Perfusion by Donald May et al., British Journal of Ophthalmology, 1983, 67.808–813.

Cold Irrigating Solution in Cataract Sugrgery May Make for Quieter Eyes, by J. Hoffman, Ocular Surgery News, Apr. 15, 1990.

Hypothermia and Viterous Surgery, by Nabil M. Jabbour, Seminars on Ophthalmology, vol. 4, No. 1 (Mar.), 1989 pp. 8–12.

Temperature–Dependent Light Damage to the Retina, by J. Rinkoff, MD, et al. American Journal of Ophthalmology 102:452–462, Oct. 1986.

Local Ocular Hypothermia in Experimental Intracular Surgery, by N. M. Jabbour, et al. pp. 1687–1690, Ophthalmoloby, Dec. 1988, vol. 95, #12.

Clinical and Histologic Effects of Extreme Intraocular Hypothermia, J. D. Zilis, et al., Americal Journal of Ophthalmology, 109:469–473.

Primary Examiner—C. Fred Rosenbaum
Assistant Examiner—Manuel Mendez
Attorney, Agent, or Firm—Cesari & McKenna

[57] ABSTRACT

The present invention provides an apparatus for heating, filtering and eliminating gas from biological fluids. The apparatus includes a heat exchanger for heating biological fluids coaxially positioned within a filter unit. The filter unit receives heated fluid from the heat exchanger within an inner chamber and vents gas to the atmosphere contained within the heated fluid through a vent on the inner chamber. The fluid is radially filtered between the inner chamber and an outer chamber by a filter element coaxially separating the inner and outer chambers.

19 Claims, 3 Drawing Sheets

APPARATUS FOR HEATING, FILTERING AND ELIMINATING GAS FROM BIOLOGICAL FLUIDS

BACKGROUND

Biological fluids such as blood stored in bags are typically heated before infusion into a patient. When heated, air bubbles form in the blood which need to be eliminated before infusion in order to prevent serious injury or death to the patient. Additionally, blood clots within the blood must be filtered from the blood before infusion.

Current methods of heating, filtering and eliminating air from biological fluids before infusion into a patient are disclosed in U.S. Pat. Nos. 4,759,749 and 4,900,308 which are issued to Verkaart. The Verkaart patents disclose an apparatus for heating, filtering and eliminating air from blood in which a heat exchanger for heating the blood is connected in series to a filter/air eliminator by a length of tubing. The filter/air eliminator receives heated blood from the heat exchanger near the top of the filter/air eliminator. Air bubbles contained within the heated blood are vented to the atmosphere through vent holes located at the top of the filter/air eliminator. The blood then travels downward through a filter element located at the bottom of the filter/air eliminator to filter blood clots from the blood.

SUMMARY OF THE INVENTION

The problem with the apparatus disclosed in the Verkaart patents is that the filter/air eliminator is not capable of processing blood at flow rates faster than the rate at which air bubbles rise upwardly within blood. This limited flow rate is caused by the downward flow rate of blood within the filter/air eliminator flowing against the air bubbles rising upwards to vent to the atmosphere. As a result, blood flowing at flow rates above the rate at which air bubbles rise will not allow air to vent to the atmosphere.

Accordingly, there is a need for an apparatus for heating, filtering and eliminating gas from biological fluids which can operate at higher flow rates than previous devices.

The present invention provides an apparatus for heating, filtering and eliminating gas from biological fluids. The apparatus includes a heat exchanger for heating biological fluids. The heat exchanger has an inlet port and an outlet passage. A filter unit surrounds a portion of the heat exchanger along the longitudinal axis of the heat exchanger. The filter unit has an inner chamber in fluid communication with the outlet passage of the heat exchanger for receiving heated biological fluid from the heat exchanger. The heated biological fluid contains gas. Top and bottom caps are included for enclosing the top and bottom of the inner and outer chambers respectively. A vent on the top cap vents the inner chamber of the filter unit to the atmosphere for venting gas from biological fluid within the inner chamber to the atmosphere. The filter unit also has an outer chamber surrounding the inner chamber. The inner chamber is coupled in fluid communication with the outer chamber via a filter element which filters biological fluid forced in a radial direction from the inner chamber into the outer chamber by biological fluid entering the inner chamber from the outlet passage of the heat exchanger.

In a preferred embodiment, the filter unit includes an outlet port in fluid communication with the outer chamber for discharging biological fluid from the filter unit. The heat exchanger includes an inner conduit through which heated water flows as a heating medium and an outer conduit coaxial with the inner conduit. The heat exchanger has a spiraling heat exchanging passageway between the inner conduit and the outer conduit such that biological fluid flowing through the heat exchanging passageway is heated. The filter element is coaxial to the heat exchanger. The filter element coaxially couples the inner chamber of the filter unit in fluid communication with the outer chamber for radially filtering biological fluid forced by incoming biological fluid from the inner chamber into the outer chamber. The biological fluid flows upwardly through the heat exchanging passageway into the inner chamber towards the vent and radially outwardly from the inner chamber into the outer chamber, and downwardly through the outer chamber.

The present invention provides an apparatus for heating, filtering and eliminating gas from biological fluids which is capable of operating at faster flow rates than obtainable with previous devices. The present invention apparatus is also more compact than pre-existing devices because the filter unit and the heat exchanger are combined into a single assembly rather than being connected to each other by a length of tubing. Therefore, a smaller volume of blood is contained within the present invention apparatus during operation than if all the components were separate. As a result, less biological fluid is wasted when the present invention apparatus is discarded after use.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1:
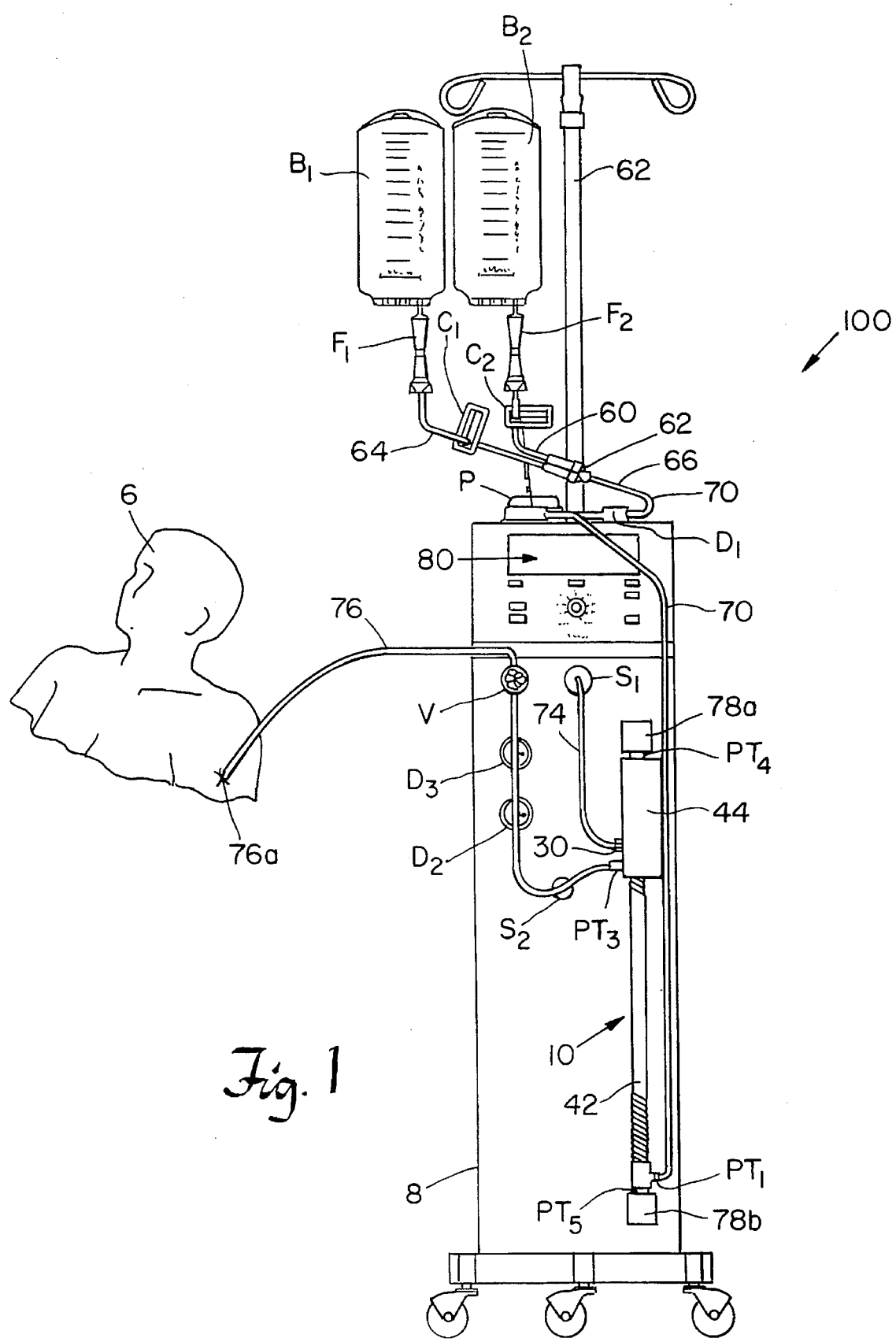
FIG. 1 is a side view of an infusion apparatus including the present invention heater-filter assembly for heating, filtering and eliminating gas from biological fluids.

In FIG. 1, infusion apparatus 100 includes a housing 8 having a control panel 80 for controlling apparatus 100. An intravenous pole 62 is affixed to housing 8. Bags $B_1$ and $B_2$, containing blood, are hung on intravenous pole 62. Bags $B_1$ and $B_2$ are in fluid communication with connector 62 via microaggregate filters $F_1$ and $F_2$, blood compatible tubing 64 and 60, and clamps $C_1$ and $C_2$ respectively. Connector 62 is in fluid communication with heater-filter assembly 10 via blood compatible tubing 70, air detector $D_1$ and inlet port $PT_1$. Air detector $D_1$ detects the presence or absence of fluid in the upper region 66 of tubing 70. Peristaltic pump P pumps blood from bags $B_1$ and $B_2$ through heater-filter assembly 10 and into patient 6.

Heater-filter assembly 10 includes a heat exchanger 42 coaxially positioned within a filter unit 44 along the same longitudinal axis. A pressure sensor $S_1$ is in fluid communication with heater-filter assembly 10 via blood compatible tubing 74 and side port 30 on filter unit 44. Pressure sensor $S_1$ senses the pressure of fluid within heater-filter assembly 10. Water input port $PT_4$ and water output port $PT_5$ on heat exchanger 42 are in fluid communication with manifolds 78a and 78b respectively, which are located on the side of housing 8. Manifolds 78a and 78b are in fluid communication with a heated water supply contained within housing 8. Water ports $PT_4$ and $PT_5$ permit heated water from the water supply to flow through heat exchanger 42. Heater-filter assembly 10 is in fluid communication with patient 6 via outlet port $PT_3$ on filter unit 44, temperature sensor $S_2$, air detector D2, air detector D3, valve V, blood compatible infusion tubing 76 and catheter (or similar device) 76a.

In operation, blood from bags $B_1$ and $B_2$ are emptied into tubing 70 via filters $F_1$ and $F_2$, tubing 64 and 62, clamps C1 and C2, and connector 62. Bags $B_1$ and $B_2$ can be emptied at the same time or separately. Air detector $D_1$ detects the presence of fluid within the upper region 66 of tubing 70 and allows apparatus 100 to operate. The blood is pumped by pump P into heater-filter assembly 10 through inlet port $PT_1$ on heat exchanger 42. Heated water flows through heat exchanger 42 downward from manifold 78a into water input port $PT_4$ and out of water output port $PT_5$ into manifold 78b to heat the blood to a suitable infusion temperature. After the blood is heated by heat exchanger 42, the heated blood enters filter unit 44. Filter unit 44 eliminates air bubbles from the blood which form during heating and filters blood clots from the blood. Once the blood has been processed by heater-filter assembly 10, the blood is infused into patient 6 via outlet port $PT_3$ on filter unit 44, temperature sensor $S_1$, air detectors $D_1$ and $D_2$, valve V, infusion tubing 76 and catheter 76a.

The pressure of the blood in the heater-filter assembly 10 is sensed by pressure sensor $S_1$ so that the pressure can be controlled or the system shut down in the event that the pressure is unsuitable for infusion. Temperature sensor $S_2$ monitors the temperature of the heated blood and feeds back information to a microprocessor to ensure that the temperature of the blood is at a proper level. Air detectors $D_2$ and $D_3$ are redundant safety features which is preferable to ensure that blood having air bubbles does not enter the patient. If air bubbles pass through infusion tubing 76, detectors $D_2$ and $D_3$ close valve V and shut down pump P, thereby terminating the flow of blood to the patient.

Figure 2:
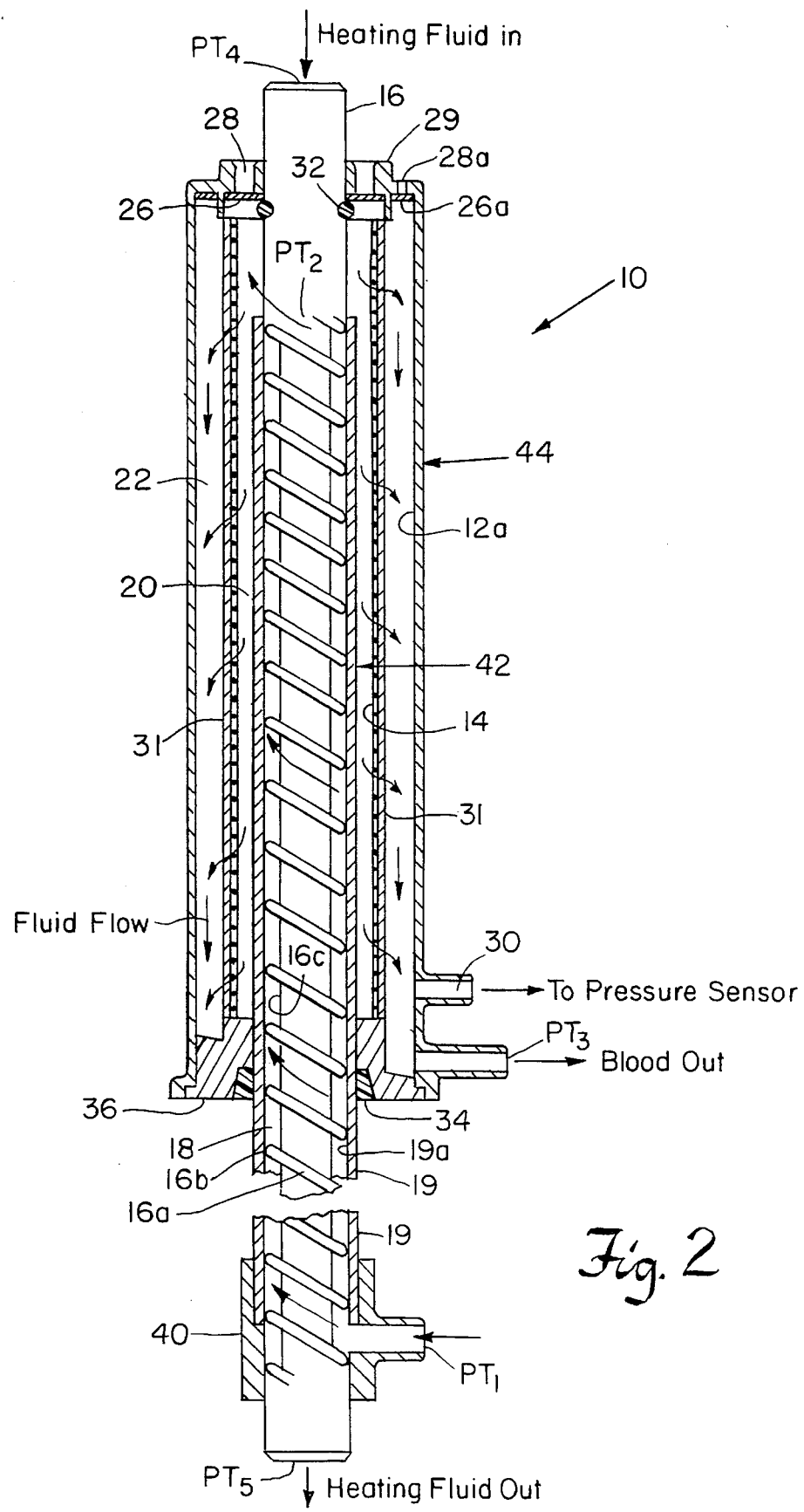
FIG. 2 is a side sectional view of the present invention heater-filter assembly.
Figure 3:
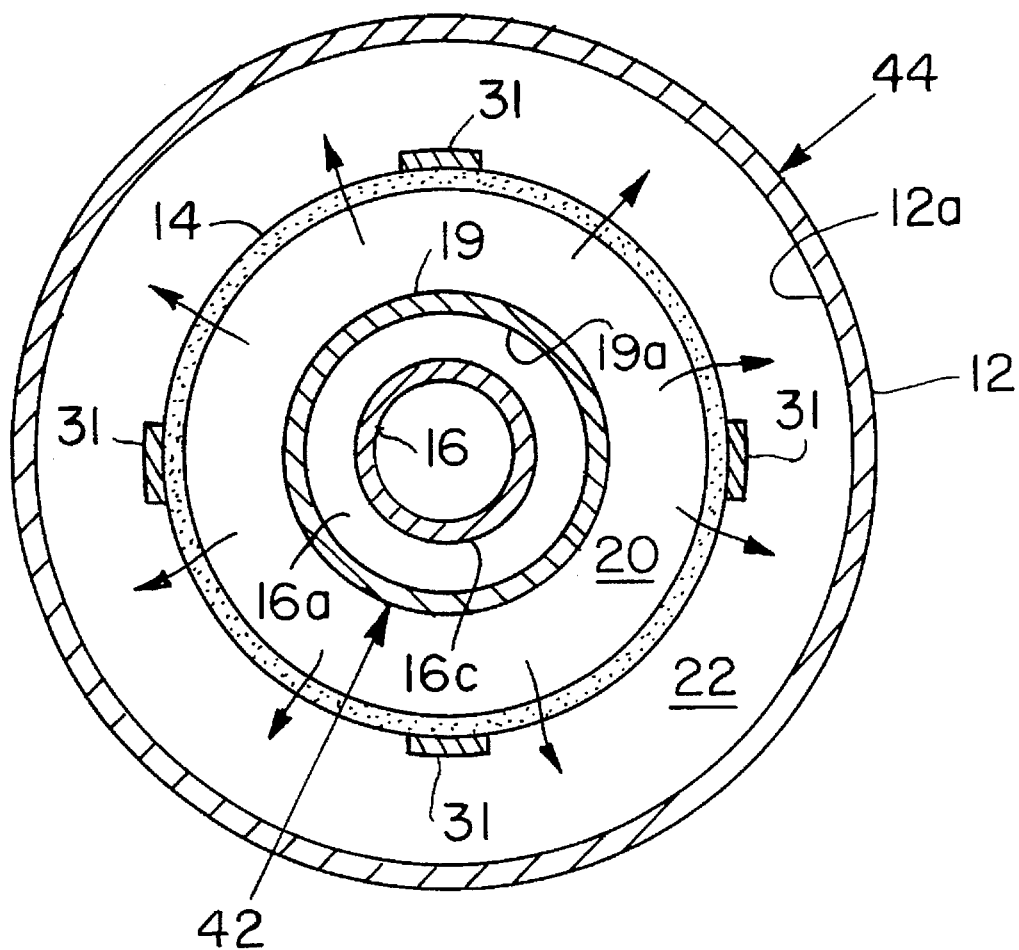
FIG. 3 is a cross-sectional view of the present invention heater-filter assembly.

FIGS. 2 and 3 depict heater-filter assembly 10 in greater detail. Heat exchanger 42 is positioned coaxial to the longitudinal axis of filter unit 44 such that an upper end of the heat exchanger 42 extends through the filter unit 44. The heat exchanging inner tube 16 of heat exchanger 42 is sealed to top cap 29 at the upper end of filter unit 44 by an O-ring 32. The outer tube 19 of heat exchanger 42 is sealed to the lower end of filter unit 44 by a bottom cap 36 and seal 34.

Heat exchanger 42 is formed by the heat exchanging inner tube 16 and the outer tube 19. Heated water enters heat exchanging inner tube 16 through water input port $PT_4$ and exits heat exchanging inner tube 16 through water output port $PT_5$. Heat exchanging inner tube 16 has spiral flutes 16a integrally formed therein. The periphery 16b of the flutes 16a contact the inner wall 19a of the outer tube 19 to form a spiral fluid passageway 18 between inner wall 19a of the outer tube 19 and the outer wall 16c of the heat exchanging inner tube 16. Passageway 18 is spiraled to increase the time that the blood is in heat exchanging contact with heat exchanging inner tube 16 for efficient heating.

End cap 40 seals outer tube 19 to heat exchanging inner tube 16, thereby preventing leakage of blood. Inlet port $PT_1$ is located within end cap 40 and is in fluid communication with passageway 18 for allowing blood to enter passageway 18. Outlet passage $PT_2$ allows heated blood to exit passageway 18 and heat exchanger 42. In the preferred embodiment, heat exchanging inner tube 16 is made of aluminum, outer tube 19 is made of clear, biocompatible plastic, and seal 34 and O-ring 32 are made of biocompatible elastomers. However, alternatively, heat exchanging inner tube 16 and outer tube 19 can be made of other suitable materials such as stainless steel.

Filter unit 44 includes a tubular housing 12 preferably formed of clear, biocompatible plastic. An inner chamber 20 defined by the annular region between heat exchanger 42, filter element 14, top cap 29 and bottom cap 36, surrounds and is in fluid communication with outlet passage $PT_2$ of heat exchanger 42. Inner chamber 20 is in fluid communication with and is coaxially separated from outer chamber 22 by a tubular filter element 14. Outer chamber 22 is the annular region defined by filter element 14, the outer wall 12a of housing 12, top cap 29 and bottom cap 36. Four equally spaced ribs 31 extending between and secured to top cap 29 and bottom cap 36 are positioned concentrically about filter element 14 to keep filter element 14 properly positioned when blood flows through filter element 14. Ribs 31 are thin enough so that the flow of blood through filter element 14 is not substantially impeded by ribs 31.

Vent holes 28 and 28a in top cap 29 vent inner chamber 20 and outer chamber 22 respectively to the atmosphere. Vent holes 28 and 28a are preferably in the form of radial slots located at the top of housing 12 extending through top cap 29. Outlet passage $PT_2$ of heat exchanger 42 is positioned near the top of inner chamber 20 and vent holes 28. Filter elements 26 and 26a cover the vent holes 28 and 28a respectively and provide a sterile barrier between the atmosphere and inner chamber 20 and outer chamber 22. Filter elements 26 and 26a are preferably a laminate of porous polytetrafluoroethylene and polyester fabric having a suitable pore size to enable the passage of air but prevent the passage of liquids and most bacteria. As a result, only gases but not blood, can exit inner chamber 20 and outer chamber 22 through vent holes 28 and 28a. Additionally, contaminants cannot enter inner chamber 20 and outer chamber 22 through vent holes 28 and 28a. Although vent holes 28 and 28a are described as radial holes, alternatively, vent holes 28 and 28a can be of other suitable configurations such as round holes or rectangular slots. Additionally, inner chamber 20 and outer chamber 22 can be vented to a vacuum instead of to the atmosphere.

A fluid outlet port $PT_3$ on filter unit 44 is in fluid communication with outer chamber 22 and allows fluid to exit outer chamber 22 and heater-filter assembly 10. Side port 30 is also in fluid communication with outer chamber 22 and is connected to pressure sensor $S_1$ via line 74 for sensing the pressure within heater-filter assembly 10. Although housing 12 is preferably made of clear biocompatible plastic, housing 12 can be made of opaque plastic or other suitable materials such as stainless steel.

A more detailed description of the operation of heater-filter assembly 10 is as follows. Heated water enters water input port $PT_4$ and exits water output port $PT_5$ of heat exchanger 42, heating heat exchanging inner tube 16. Blood is pumped by pump P (FIG. 1) and enters heat exchanger 42 through inlet port $PT_1$ in end cap 40. The blood enters spiral passageway 18 and is pumped upwardly through heat exchanger 42 within spiral passageway 18. The blood is heated as it passes over the outer wall 16c of heat exchanging inner tube 16. The heated blood exits passageway 18 at outlet passage $PT_2$ and enters inner chamber 20. Air bubbles forming within the heated blood in heat exchanger 42 rise upwards and are carried upwards within the rising blood towards vent holes 28. The air bubbles are vented from inner chamber 20 to the atmosphere through filter element 26 and vent holes 28. Since the upwardly rising air bubbles are also carried upwards towards vent holes 28 by the rising blood, the flow rate of blood through heater-filter assembly 10 is not limited to the speed at which bubbles rise. As a result, heater-filter assembly 10 can operate at flow rates of at least 6 liters/min. The blood within inner chamber 20 is then forced downward within inner chamber 20 and radially outward into outer chamber 22 through filter element 14 by additional blood entering inner chamber 20 from outlet passage $PT_2$. Filter element 14 filters out blood clots and any other undesirable particulates from the blood. Any remaining air bubbles within the blood can exit outer chamber 22 via filter element 26a and vent hole 28a. The processed blood is discharged from outer chamber 22 and heater-filter assembly 10 via outlet port $PT_3$ on filter unit 44. In the preferred embodiment, filter element 14 is a 40 micron filter. However, alternatively, the pore size of filter element 14 can be varied. Additionally, although the flow of blood from inner chamber 20 through filter element 14 into outer chamber 22 is depicted to flow radially outward in all directions (360°), the blood can be limited to flow radially outward in directions which are less than 360°.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. For example, although the present invention apparatus has been described for heating, filtering and eliminating gas from blood, the present invention apparatus may be used to heat, filter and eliminate gas from any fluid or mixture of fluids. Additionally, the inner chamber 20, outer chamber 22 and filter element 14 of the filter unit do not have to be coaxial with the heat exchanger 42 but can be eccentric in relation to each other. Furthermore, inner heat exchanging tube 16 may be replaced with an electric heating element. A contained water jacket surrounding the electric heating element can be employed to dissipate any hot spots on the electric heating element in order to provide a heat exchanging surface of uniform temperature. Also, filter element 14 does not have to be tubular in shape but can be rectangular or polygonal in shape.

What is claimed is:

1. Apparatus comprising:
   a heat exchanger having a longitudinal axis for heating biological fluids, the heat exchanger having an inlet port and an outlet passage; and
   a filter unit, the filter unit surrounding a portion of the heat exchanger along the longitudinal axis, the filter unit comprising:
      an inner chamber, the inner chamber being in fluid communication with the outlet passage of the heat exchanger for receiving heated fluid from the heat exchanger, said heated fluid contains gas;
      an outer chamber surrounding the inner chamber, the inner and outer chambers having a top and a bottom;
      a top cap enclosing the top of the inner and outer chambers;
      a bottom cap enclosing the bottom of the inner and outer chambers;
      a vent on the top cap venting the inner chamber for venting the gas from heated fluid within the inner chamber; and
      a filter element coupling the inner and outer chambers together in fluid communication, the filter element for filtering fluid pumped in a radial direction from the inner chamber to the outer chamber.

2. The apparatus of claim 1 in which the filter unit further comprises an outlet port in fluid communication with the outer chamber for discharging the fluid from the filter unit.

3. The apparatus of claim 1 in which the heat exchanger comprises:
   an inner conduit containing a heating medium; and
   an outer conduit coaxial with the inner conduit forming a heat exchanging passageway between the inner conduit and the outer conduit such that fluid flowing through the heat exchanging passageway is heated.

4. The apparatus of claim 3 in which the heating medium is heated water flowing through the inner conduit.

5. The apparatus of claim 3 in which the heat exchanging passageway is spiraled.

6. The apparatus of claim 1 in which the filter element is coaxial to the heat exchanger, the filter element coaxially coupling the inner chamber in fluid communication with the outer chamber for radially filtering fluid.

7. The apparatus of claim 6 in which the fluid flows upwardly through the heat exchanging passageway into the inner chamber towards the vent, radially and outwardly from the inner chamber into the outer chamber, and downwardly through the outer chamber.

8. Apparatus comprising:
   a heat exchanger having a longitudinal axis for heating biological fluids, the heat exchanger having an inlet port and an outlet passage; and
   a filter unit coaxially surrounding a portion of the heat exchanger along the longitudinal axis, the filter unit comprising:
      an inner chamber, the inner chamber being in fluid communication with the outlet passage of the heat exchanger for receiving heated fluid from the heat exchanger, said heated fluid containing gas;
      an outer chamber coaxially surrounding the inner chamber, the inner and outer chambers having a top and a bottom;
      a top cap enclosing the top of the inner and outer chambers;
      a bottom cap enclosing the bottom of the inner and outer chambers;
      a vent on the top cap venting the inner chamber to the atmosphere for venting gas from heated fluid within the inner chamber to the atmosphere; and
      a filter element coaxially coupling the inner and outer chambers together in fluid communication, the filter element radially filtering fluid pumped in a radial direction from the inner chamber into the outer chamber, the fluid in the apparatus flowing upwardly through the heat exchanging passageway into the inner chamber towards the vent, radially and outwardly from the inner chamber into the outer chamber, and downwardly through the outer chamber.

9. The apparatus of claim 8 in which the filter assembly further comprises an outlet port in fluid communication with the outer chamber for discharging the fluid from the filter unit.

10. The apparatus of claim 8 in which the heat exchanger comprises:
    an inner conduit containing a heating medium; and
    an outer conduit coaxial with the inner conduit forming a heat exchanging passageway between the inner conduit and the outer conduit such that fluid flowing through the heat exchanging passageway is heated.

11. The apparatus of claim 10 in which the heating medium is heated water flowing through the inner conduit.

12. The apparatus of claim 10 in which the heat exchanging passageway is spiraled.

13. A method of processing biological fluids comprising the steps of:

heating a biological fluid with a heat exchanger having a longitudinal axis;

discharging the heated fluid from the heat exchanger into an inner chamber of a filter unit, the inner chamber of the filter unit surrounding a portion of the heat exchanger along the longitudinal axis;

eliminating gas from the heated fluid within the inner chamber of the filter unit by venting the gas through a vent on the inner chamber; and filtering the fluid by forcing the fluid from the inner chamber into an outer chamber in a radial direction through a filter element, the outer chamber surrounding the inner chamber and coupled in fluid communication with the inner chamber by the filter element.

14. The method of claim 13 further comprising the step of infusing the fluid into a patient.

15. The method of claim 13 further comprising the step of pumping biological fluid to be processed into the heat exchanger with a pump.

16. The method of claim 13 in which the filter element coaxially couples the inner chamber in fluid communication with the outer chamber for radially filtering the fluid.

17. The method of claim 16 in which the fluid flows upwardly through the heat exchanger into the inner chamber towards the vent, radially from the inner chamber into the outer chamber, and downwardly through the outer chamber.

18. A method of processing biological fluids comprising the steps of:

pumping biological fluid to be processed with a pump into a heat exchanger having a longitudinal axis;

heating the biological fluid with the heat exchanger;

discharging the heated fluid from the heat exchanger into an inner chamber of a filter unit, the inner chamber of the filter unit coaxially surrounding a portion of the heat exchanger along the longitudinal axis;

eliminating gas from the heated fluid within the inner chamber of the filter unit by venting the gas to the atmosphere through a vent on the inner chamber;

filtering the fluid by forcing the fluid from the inner chamber into an outer chamber in a radial direction through a filter element, the outer chamber coaxially surrounding the inner chamber and coupled in fluid communication with the inner chamber by the filter element; and infusing the fluid into a patient.

19. The method of claim 18 in which the fluid flows upwardly through the heat exchanger into the inner chamber towards the vent, radially from the inner chamber into the outer chamber, and downwardly through the outer chamber.

* * * * *